(12) United States Patent
Goget et al.

(10) Patent No.: US 7,358,279 B2
(45) Date of Patent: Apr. 15, 2008

(54) EMULSIONS OF OIL-IN-WATER FOR COSMETIC AND PHARMACEUTICAL COMPOSITIONS

(75) Inventors: Caroline Goget, Paris (FR); Ulrich Issberner, Ambler, PA (US); Rolf Kawa, Monheim (DE); Joerg Sorns, Duesseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 11/630,070

(22) PCT Filed: Jun. 18, 2005

(86) PCT No.: PCT/EP2005/006601

§ 371 (c)(1),
(2), (4) Date: Jun. 13, 2007

(87) PCT Pub. No.: WO2006/000360

PCT Pub. Date: Jan. 5, 2006

(65) Prior Publication Data

US 2007/0248632 A1    Oct. 25, 2007

(30) Foreign Application Priority Data

Jun. 29, 2004    (DE) .................... 10 2004 031 550

(51) Int. Cl.
*A01N 43/04*    (2006.01)
*A61K 7/00*    (2006.01)
*A61K 9/14*    (2006.01)

(52) U.S. Cl. .................. 514/937; 514/23; 424/401; 424/489

(58) Field of Classification Search ................ 424/401, 424/489; 514/23, 937
See application file for complete search history.

(56) References Cited

U.S. PATENT DOCUMENTS

| | | | |
|---|---|---|---|
| 5,795,978 | A | 8/1998 | Ansmann et al. |
| 5,958,431 | A | 9/1999 | Brancq et al. |
| 2004/0029977 | A1 | 2/2004 | Kawa et al. |
| 2004/0116542 | A1 | 6/2004 | Baumoeller et al. |
| 2005/0025957 | A1 | 2/2005 | Issberner et al. |
| 2005/0136081 | A1 | 6/2005 | Kawa et al. |

FOREIGN PATENT DOCUMENTS

| | | |
|---|---|---|
| DE | 103 46 515 A1 | 4/2005 |
| DE | 103 47 940 A1 | 5/2005 |
| EP | 0 553 241 B1 | 4/1995 |
| EP | 1 247 519 A1 | 10/2002 |
| WO | WO 97/18033 A1 | 5/1997 |
| WO | WO 02/43672 A1 | 6/2002 |
| WO | WO 02/056841 A2 | 7/2002 |

*Primary Examiner*—Johann R. Richter
*Assistant Examiner*—Konata M. George
(74) *Attorney, Agent, or Firm*—John F. Daniels

(57) ABSTRACT

Emulsions suitable for use in cosmetic and pharmaceutical compositions are disclosed. Various substrates for body care, such as wipes and pads, are disclosed, which substrates are impregnated with the emulsions. Such treated substrates are suitable for use, for example, in body care, sun protection, antiperspirant and insect repellent formulations. A process for cold temperature production of the emulsions is also disclosed.

14 Claims, No Drawings

EMULSIONS OF OIL-IN-WATER FOR COSMETIC AND PHARMACEUTICAL COMPOSITIONS

CROSS-REFERENCE TO RELATED APPLICATIONS

This application is a national phase filing under 35 U.S.C. § 371 and claims priority to International Application No. PCT/EP2005/006601 which has an International filing date of Jun. 18, 2005, and which designated the United States of America and which claims priority to German Application No. 10 2004 031 550.7, filed Jun. 29, 2004, the entire disclosures of which are hereby incorporated herein by reference.

FIELD OF THE INVENTION

This invention relates to concentrated, transparent, self-emulsifying emulsion bases/concentrates flowable at 23° C. which are used for the production of cosmetic or pharmaceutical emulsions.

BACKGROUND OF THE INVENTION

So-called self-emulsifying emulsion bases for the production of oil-in-water emulsions contain emulsifiers, oil components and waxes in quantities adapted to one another. The products in question are normally water-free products with a wax-like to solid consistency of which the melting points/melting ranges depend, inter alia, upon the waxes and oil components used, but which generally have melting points of at least 30° C. By using systems such as these, cosmetic chemists save themselves time-consuming tests in the development of cosmetic emulsions. At the same time, the customer enjoys lower costs for warehousing and raw materials testing. Self-emulsifying bases based on fatty alcohols and alkyl oligoglycosides are disclosed, for example, in EP 553 241 A1 and WO 97/18033. Typical self-emulsifying bases are obtainable from Cognis under the names of Emulgade® CL and Emulgade® CBN. To produce emulsions, 10 to 20 parts of these concentrates (self-emulsifying bases) are generally heated, if desired together with other oil components, to a temperature 20° C. above the melting temperature of the self-emulsifying bases and emulsified with 80 parts water also heated to that temperature, optionally followed by the addition of other auxiliaries, such as preservatives, perfume or active components. Emulsions usually having a droplet diameter of $\geq 10$ µm are formed in this way. In order to avoid sedimentation, experience has shown that the viscosity of such emulsions should be >5,000 mPa·s (Brookfield RVF, spindle 5, 10 r.p.m at 23° C.). The scope of application of such concentrates is clearly limited. They are not suitable where processing in an energy-saving cold process is envisaged or where low-viscosity emulsions with a viscosity of $\leq 1,000$ mPa·s are to be developed for use as roll-ons, sprays or as impregnating liquids for wet wipes.

Besides so-called self-emulsifying bases, emulsion concentrates are also commercially available which likewise contain the key constituents of an emulsion, namely emulsifiers, oil components and waxes, and which have a water content of about 60%. These concentrates are typically produced by the PIT process and, accordingly, have a mean droplet diameter of <1 µm and often between 100 nm and 500 nm. They may readily be diluted with cold water and are particularly suitable for the production of roll-on concepts, sprays or as an impregnating liquid for wipes. In combination with viscosity-generating polymers, lotions and creams can also be produced. The disadvantage is that other oil components can only be added with intensive homogenization. In addition, such emulsion concentrates are microbiologically susceptible and cannot be economically transported on account of their high water content. In addition, the PIT concentrates in question can normally only be produced on the basis of ethoxylated emulsifiers. Unfortunately, this class of emulsifiers is being increasingly discussed in negative terms for dermatological and ecological reasons. So-called "ethoxylate-free" nanoemulsions, albeit with a relatively high water content, are known from DE 103 46 515 while ethoxylate-free self-emulsifying bases are known from DE 103 47 940. O/W emulsions with a low water content, i.e. basically concentrates, are known from WO 02/056841. However, these emulsions, which have a water content of at most 30%, can have the disadvantage that they are not stable in storage at >30° C. and also cannot be emulsified with other oil components without relatively high energy consumption.

Accordingly, the problem addressed by the present invention was to provide self-emulsifying emulsion bases or concentrates which would be liquid and hence cold-processable, would have a low water content, could readily be emulsified with other oil components and could be further diluted with water without any separation occurring. Ideally, such concentrates would be present as transparent solutions because, in contrast to conventional liquid emulsion concentrates, systems such as these would have improved long-term stability.

BRIEF SUMMARY OF THE INVENTION

It has surprisingly been found that the problem stated above is addressed by compositions which comprise mixtures containing lauryl glucoside, myristyl glucoside, polyglycerol-2-dipolyhydroxystearate, cetyl alcohol, stearyl alcohol and thinly liquid oil components in effective amounts with up to 10% by weight water. Such mixtures are transparent and can readily be emulsified with other oil components and diluted with water without any separation occurring.

Accordingly, the present invention relates to a composition containing:

(a) 3 to 5% by weight lauryl glucoside,
(b) 1 to 2% by weight myristyl glucoside,
(c) 5 to 7% by weight polyglycerol-2-dipolyhydroxystearate,
(d) 4 to 8% by weight $C_{12-24}$ fatty alcohols,
(e) 70 to 75% by weight oil components,
(f) 4 to 5% by weight of a hydrotrope selected from diols, polyols or from glycerol, and mixtures thereof, and
(g) 2 to 10% by weight water.

The compositions are flowable at 23° C., i.e. they preferably have a viscosity of less than 2,000 mPa·s at 23° C. (Brookfield RVF, spindle 5, 10 r.p.m.). The emulsion bases are preferably transparent. In another preferred embodiment, they have a mean particle size of at most 100 nm, preferably below 50 nm and more particularly below 10 nm. The compositions are so-called micellar solutions.

In one preferred embodiment, the $C_{12-14}$ fatty alcohols are selected from cetyl alcohol or stearyl alcohol, or a combination of these two fatty alcohols. In another preferred embodiment, the hydrotrope is glycerol.

Accordingly, a particularly preferred embodiment contains:
(a) 3 to 5% by weight lauryl glucoside,
(b) 1 to 2% by weight myristyl glucoside,
(c) 5 to 7% by weight polyglycerol-2-dipolyhydroxystearate,
(d) 4 to 8% by weight stearyl alcohol or cetyl alcohol or any combination of these two fatty alcohols,
(e) 70 to 75% by weight oil components,
(f) 4 to 5% by weight glycerol and
(g) 2 to 10% by weight water.

It has been found that mixtures in the ratio indicated and based on these raw materials show the desired properties. Otherwise, the mixtures turn cloudy and very quickly separate, can no longer be readily emulsified, i.e. without a homogenization step, with other oil components and cream up immediately when diluted with water. Preferred oil components include water-insoluble organic compounds which are liquid at 25° C. and have a viscosity of 1 to 100 mPa·s. Thinly liquid oil components with a viscosity of 1 to 50 mPa·s are particularly preferred.

DETAILED DESCRIPTION OF THE INVENTION

The concentrates according to the invention can be diluted with 30 to 95 parts water per 1 part concentrate and may be used for the production of sprays, roll-on concepts, wet wipe impregnating liquids and—using polymers—for the formulation of lotions and/or creams.

Accordingly, the present invention relates to cosmetic preparations containing 5 to 40% by weight of the concentrates according to the invention. The cosmetic preparations are preferably o/w emulsions. The present invention also relates to the use of the emulsion concentrates according to the invention for impregnating cosmetic wipes and wet wipes and to their use for the production of body care formulations, sun protection formulations, antiperspirant formulations and insect repellent formulations. The present invention also relates to wipes and pads impregnated with the emulsion concentrate according to the invention or with an emulsion containing 5 to 40% by weight of the emulsion concentrate. By virtue of their particle fineness and their transparency, these emulsion concentrates, and also the emulsions according to the invention obtained from them, are particularly suitable for the impregnation of various different absorbent substrates. Examples of such coated substrates are wipes for body care and intimate hygiene, make-up wipes, coated cottonwool pads, wipes impregnated with sun protection formulations or insect repellent formulations, etc.

The present invention also relates to a process for the cold production of emulsions in which an oil phase optionally containing other oil-soluble components and a water phase optionally containing other water-soluble active components are added to the emulsifier concentrate according to the invention and dispersed or emulsified therein with simple mechanical stirring, the emulsifying process taking place at temperatures of 15 to 40° C. and preferably at temperatures of 20 to 30° C. There is no need to apply shear forces, simple mechanical stirring being sufficient. If desired, viscosity can be adjusted by addition of polymers.

Oil Components

The cosmetic or pharmaceutical preparations according to the invention contain an aqueous phase and an oil phase which may both contain other auxiliaries and additives. However, by virtue of the composition of the emulsifier concentrate and its high oil content, it is optional to add other oil components. The concentrate may be diluted solely with an aqueous phase. The percentage content of aqueous phase, including water-soluble active components, is typically in the range from 50 to 95% by weight, based on the composition as a whole, and the percentage content of oil phase in the range from 5 to 50% by weight, based on the overall composition of the end product. The oil phase may be comprised of an oil component or a mixture of oil components and of oil-soluble active components.

Suitable oil components are, for example, the classes of compounds mentioned in the following: Guerbet alcohols based on fatty alcohols containing 6 to 18 and preferably 8 to 10 carbon atoms, for example 2-ethylhexanol or 2-octyl dodecanol; esters of linear or branched, saturated or unsaturated $C_{6-24}$ fatty acids with linear or branched, saturated or unsaturated $C_{6-24}$ fatty alcohols. The following are suitable by way of example: hexyl laurate, myristyl isostearate, myristyl oleate, cetyl isostearate, cetyl oleate, stearyl isostearate, stearyl oleate, isostearyl myristate, isostearyl palmitate, isostearyl stearate, isostearyl isostearate, isostearyl oleate, oleyl myristate, oleyl isostearate, oleyl oleate, oleyl erucate, erucyl isostearate, cococaprylate/caprate. Other suitable esters are, for example, esters of $C_{18-38}$ alkylhydroxycarboxylic acids with linear or branched, saturated or unsaturated $C_{6-22}$ fatty alcohols, esters of linear and/or branched, saturated or unsaturated fatty acids with polyhydric alcohols (for example propylene glycol, dimer diol or trimer triol) and/or Guerbet alcohols, triglycerides or triglyceride mixtures, mono-, di- and tri-glyceride mixtures, esters of $C_{6-22}$ fatty alcohols and/or Guerbet alcohols with aromatic carboxylic acids, more particularly benzoic acid (for example Finsolv® TN), esters of $C_{2-12}$ dicarboxylic acids with linear or branched, saturated or unsaturated alcohols containing 1 to 22 carbon atoms or polyols containing 2 to 10 carbon atoms and 2 to 6 hydroxyl groups. Also suitable are vegetable oils, triglyceride mixtures, substituted cyclohexanes, linear symmetrical or nonsymmetrical dialkyl carbonates (for example Cetiol® OE), Guerbet carbonates based on fatty alcohols containing 6 to 18 and preferably 8 to 10 carbon atoms, linear or branched, symmetrical or nonsymmetrical dialkyl ethers containing 6 to 22 carbon atoms per alkyl group such as, for example, Di-n-octyl Ether (Cetiol® OE) or ring opening products of epoxidized fatty acid esters with polyols, hydrocarbons, such as paraffin or mineral oils, silicone oils and oligo- or poly-α-olefins. The dialkyl carbonates and dialkylethers may be symmetrical or nonsymmetrical, branched or unbranched, saturated or unsaturated and may be produced by reactions well-known from the prior art. Suitable silicone compounds are, for example, dimethyl polysiloxanes, methylphenyl polysiloxanes, cyclic silicones (cyclomethicone) and amino-, fatty acid-, alcohol-, polyether-, epoxy-, fluorine-, glycoside- and/or alkyl-modified silicone compounds. Simethicones are also suitable, being mixtures of dimethicones with an average chain length of 200 to 300 dimethyl siloxane units and hydrogenated silicates.

Linear hydrocarbons with a chain length of 8 to 40 carbon atoms, which may be branched or unbranched, saturated or unsaturated, may also be used in accordance with the invention. Of these, branched, saturated $C_{8-40}$ alkanes are preferred. Both pure substances and mixtures may be used. The mixtures are normally mixtures of different isomeric compounds. Compositions containing $C_{10-30}$, preferably $C_{12-20}$ and, more particularly, $C_{16-20}$ alkanes are particularly suitable and, of these, a mixture of alkanes containing at least 10% by weight branched alkanes, based on the total quantity of alkanes, is particularly preferred. The alkanes are preferably branched, saturated alkanes. Mixtures of alkanes containing more than 1 % by weight 5,8-diethyl dodecane and/or more than 1% by weight dodecene are particularly suitable.

Other Optional Auxiliaries and Additives

Depending on their intended application, the final cosmetic formulations contain a number of other auxiliaries and additives such as, for example, thickeners, superfatting agents, stabilizers, polymers, lecithins, phospholipids, biogenic agents, UV protection factors, antioxidants, deodorants, film formers, swelling agents, insect repellents, hydrotropes, solubilizers, preservatives, perfume oils, dyes, etc. which are listed by way of example in the following. Other emulsifiers could also be added if so desired. The quantities in which the particular additives are used is determined by the intended use.

Suitable thickeners are, for example, Aerosil® types (hydrophilic silicas), polysaccharides, more especially xanthan gum, guar-guar, agar-agar, alginates and tyloses, carboxymethyl cellulose and hydroxyethyl and hydroxypropyl cellulose, polyvinyl alcohol, polyvinyl pyrrolidone and bentonites such as, for example, Bentone® GelVS-5PC (Rheox).

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. Typical UV-A filters are, in particular, derivatives of benzoyl methane. The UV-A and UV-B filters may of course also be used in the form of mixtures, for example combinations of the derivatives of benzoyl methane, for example 4-tert.butyl4'-methoxydibenzoylmethane (Parsol® 1789) and 2-cyano-3,3-phenylcinnamic acid-2-ethyl hexyl ester (Octocrylene), and esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are often combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide. Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin.

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prunus extract, bambara nut extract, and vitamin complexes.

Deodorizing agents counteract, mask or eliminate body odors. Body odors are formed through the action of skin bacteria on apocrine perspiration which results in the formation of unpleasant-smelling degradation products. Accordingly, suitable deodorizing agents are germ inhibitors, enzyme inhibitors, odor absorbers or odor maskers.

Suitable insect repellents are, for example, N,N-diethyl-m-toluamide, pentane-1,2-diol or 3-(N-n-butyl-N-acetylamino)-propionic acid ethyl ester), which is marketed as Insect Repellent® 3535 by Merck KGaA, and Butylacetylaminopropionate.

A suitable self-tanning agent is dihydroxyacetone. Suitable tyrosine inhibitors which prevent the formation of melanin and are used in depigmenting agents are, for example, arbutin, ferulic acid, koji acid, coumaric acid and ascorbic acid (vitamin C).

Suitable preservatives are, for example, phenoxyethanol, formaldehyde solution, parabens, pentanediol or sorbic acid and the silver complexes known under the name of Surfacine® and the other classes of compounds listed in Appendix 6, Parts A and B of the Kosmetikverordnung ("Cosmetics Directive").

Suitable perfume oils are mixtures of natural and synthetic perfumes. Natural perfumes include the extracts of blossoms, stems and leaves, fruits, fruit peel, roots, woods, herbs and grasses, needles and branches, resins and balsams. Animal raw materials, for example civet and beaver, and synthetic perfume compounds of the ester, ether, aldehyde, ketone, alcohol and hydrocarbon type, are also suitable.

Suitable dyes are any of the substances suitable and approved for cosmetic purposes. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). These dyes are normally used in concentrations of 0.001 to 0.1% by weight, based on the mixture as a whole.

The following Examples relate to the emulsifier concentrates and emulsions according to the invention which are produced on the basis of the emulsifier compositions according to the invention. The Examples are illustrative of the invention and should not be construed as limiting the scope thereof.

EXAMPLES

Formulations 1-4 in Table 1 represent Examples according to the invention. Formulations C1-C3, which lie outside the limits according to the invention, are intended for comparison. The figures represent % by weight, based on the composition as a whole.

TABLE 1

| Ingredients | 1 | 2 | 3 | 4 | C1 | C2 | C3 |
|---|---|---|---|---|---|---|---|
| Lauryl glucoside | 4.2 | 4.6 | 3.8 | 4.9 | 2.8 | 4.2 | 5.3 |
| Myristyl glucoside | 1.7 | 1.4 | 1.3 | 1.8 | 1.2 | 1.7 | — |
| Polyglycerol-2-di-polyhydroxystearate | 6.0 | 6.0 | 5.4 | 6.4 | 6.0 | 6.0 | 5.3 |

TABLE 1-continued

| Ingredients | 1 | 2 | 3 | 4 | C1 | C2 | C3 |
|---|---|---|---|---|---|---|---|
| Myristyl alcohol | — | — | — | — | — | 3.5 | — |
| Cetyl alcohol | 2.2 | 2.5 | 6.0 | — | 2.2 | — | — |
| Stearyl alcohol | 2.3 | 2.5 | — | 6.0 | 2.3 | — | — |
| Glyceryl stearate | — | — | — | — | — | — | 3.0 |
| Cocoglyceride | 36.0 | 30.0 | — | — | 36.0 | 36.0 | 30.0 |
| Dicaprylyl carbonate | 38.0 | 12.0 | — | — | 38.0 | 38.0 | 30.0 |
| Octyl dodecanol | — | — | 30.0 | — | — | — | — |
| Cetearyl isononanoate | — | 15.0 | — | 32.0 | — | — | — |
| Caprylic/Capric Triglyceride | — | 15.0 | 30.0 | — | — | — | — |
| Isopropyl myristate | — | — | — | 25.0 | — | — | — |
| Mineral Oil | — | — | 13.0 | 13.0 | — | — | — |
| Glycerol | 4.5 | 4.5 | 4.5 | 4.5 | 4.5 | 4.5 | 4.0 |
| Water | 5.1 | 6.5 | 6.0 | 6.4 | 7.0 | 6.1 | 22.4 |
| Appearance | Transparent | Transparent | Transparent | Transparent | Cloudy | Transparent | Cloudy |
| Phase stability 4 weeks RT/40° C. | + | + | + | + | − | + | − |
| Dilutable with H$_2$O | Homogeneous | Homogeneous | Homogeneous | Homogeneous | Separation | Separation | Yes |
| Dilutable with oil | Yes | Yes | Yes | Yes | Yes | Yes | Separation |

The results show that only the Examples according to the invention are phase-stable and/or can be further processed without difficulty.

The following Examples describe the commercial application of the concentrates according to the invention. The figures represent % by weight, based on the composition as a whole.

1. Application for Wet Wipe Concepts

The wipes can be sprayed or even impregnated. Quantities of about 3 g of the following emulsions (Examples 1a, 1b, 1c) were applied per 1 g wipe. Wipe material: spunlace viscose 65%/polyester 35% -55 g/m$^2$.

| | | |
|---|---|---|
| 1a. | Concentrate Example 1 | 10.0% by weight |
| | water, preservative | 90% by weight |
| 1b. | Concentrate Example 1 | 8.0% by weight |
| | cetearyl isononanoate | 4.0% by weight |
| | water, preservative | 88.0% by weight |
| 1c. | Concentrate Example 3 | 4.0% by weight |
| | tocopherol | 0.5% by weight |
| | water, preservative | 95.5% by weight |

2. Application for Skin Care Concepts

| | | |
|---|---|---|
| 2a. | Body spray | |
| | Concentrate Example 2 | 12.0% by weight |
| | water, preservative | 88.0% by weight |
| 2b. | Body lotion | |
| | Concentrate Example 4 | 10.0% by weight |
| | Dicaprylyl carbonate | 10.0% by weight |
| | Vitamin F | 2.0% by weight |
| | Sodium polyacrylate | 0.7% by weight |
| | water, preservative | 77.3% by weight |
| 2c. | Sun spray | |
| | Concentrate Example 1 | 15.0% by weight |
| | Dicaprylyl carbonate | 5.0% by weight |
| | Cosmedia ® DC | 2.0% by weight |
| | Ethylhexyl methoxycinnamate | 7.5% by weight |
| | Butylmethoxy dibenzoyl methane | 2.5% by weight |
| | Sodium polyacrylate | 0.1% by weight |
| | Water, preservative | 67.9% by weight |
| 2d. | Self-tanning spray | |
| | Concentrate Example 4 | 10.0% by weight |
| | Dicaprylyl carbonate | 10.0% by weight |
| | Vitamin E | 2.0% by weight |
| | Sodium polyacrylate | 0.7% by weight |
| | Dihydroxyacetone | 4.0% by weight |
| | Water, preservative | 73.3% by weight |
| 2e. | Insect repellent spray | |
| | Concentrate Example 1 | 10.0% by weight |
| | Dicaprylyl carbonate | 10.0% by weight |
| | Vitamin E | 2.0% by weight |
| | Sodium polyacrylate | 0.7% by weight |
| | Ethylbutylacetyl aminopropionate | 8.0% by weight |
| | Water, preservative | 69.3% by weight |

3. Application for AP/deo Concepts

| | | |
|---|---|---|
| 3a. | AP/deo spray | |
| | Concentrate Example 3 | 10.0% by weight |
| | Dicaprylyl carbonate | 10.0% by weight |
| | Triethyl citrate | 2.0% by weight |
| | Vitamin E | 2.0% by weight |
| | Aluminium chlorohydrate | 6.0% by weight |
| | Water, preservative | 70.0% by weight |
| 3b. | AP/deo roll on | |
| | Concentrate Example 3 | 10.0% by weight |
| | Dicaprylyl carbonate | 10.0% by weight |
| | Triethyl citrate | 2.0% by weight |
| | Vitamin E | 2.0% by weight |
| | Hydroxypropyl cellulose | 0.5% by weight |
| | Aluminium chlorohydrate | 6.0% by weight |
| | Water, preservative | 69.5% by weight |
| 3c. | AP/deo roll on | |
| | Concentrate formulation 3 | 15% by weight |
| | Cyclomethicone | 10% by weight |
| | Triethyl citrate | 4% by weight |
| | Vitamin E | 1% by weight |
| | Hydroxypropyl cellulose | 0.5% by weight |
| | Aluminium-zirconium tetrachlorohydrate | 10% by weight |
| | Water, preservative | 59.5% by weight |

In the above Examples, Phenonip, Euxyl K 702 and Symdiol 68 were used as preservatives.

4. Application for Body Care Concepts

| 4a. | Body cream | |
|---|---|---|
| | Concentrate formulation 4 | 25% by weight |
| | Dicaprylyl ether | 5% by weight |
| | Sodium polyacrylate | 1.5% by weight |
| | Aluminium starch octenyl succinate | 1% by weight |
| | Glycerol | 3% by weight |
| | Water, preservative | 64.5% by weight |
| 4b. | Body lotion | |
| | Concentrate formulation 4 | 20% by weight |
| | Cyclomethicone | 4% by weight |
| | Cosmedia DC | 1.5% by weight |
| | (Hydrogenated Dimer Dilinoleyl/ Dimethylcarbonate Copolymer) | |
| | Carbomer | 0.5% by weight |
| | Glycerol | 2% by weight |
| | Water, preservative | 72% by weight |
| 4c. | Body lotion | |
| | Concentrate formulation 4 | 20% by weight |
| | Hydrogenated polyisobutene | 4% by weight |
| | Carbomer | 0.5% by weight |
| | Glycerol | 3% by weight |
| | Water, preservative | 72.5% by weight |

5. Application for Sun Protection Concepts

| 5a. | Sun lotion | |
|---|---|---|
| | Concentrate formulation 1 | 25% by weight |
| | Titanium dioxide, nanoized | 3% by weight |
| | Zinc oxide, nanoized | 4% by weight |
| | Cosmedia DC | 1% by weight |
| | Glycerol | 3% by weight |
| | Water, preservative | 64% by weight |
| 5b. | Sun cream | |
| | Concentrate formulation 2 | 25% by weight |
| | Dibutyl adipate | 5% by weight |
| | Ethylhexyl triazone | 2% by weight (Uvinul T 150) |
| | Diethylaminohydroxybenzoyl hexyl benzoate | 2% by weight (Uvinul A plus) |
| | Ethylhexyl methoxycinnamate | 6% by weight (Neo Heliopan AV) |
| | Cosmedia DC (Hydrogenated Dimer Dilinoleyl/ Dimethylcarbonate Copolymer) | 1% by weight |
| | Sodium polyacrylate | 1% by weight |
| | Glycerol | 3% by weight |
| | Water, preservative | 55% by weight |
| 5c. | Sun lotion | |
| | Concentrate formulation 1 | 25% by weight |
| | Dibutyl adipate | 3% by weight |
| | Diethylhexyl butamidotriazone | 2% by weight (Uvasorb HEB) |
| | Ethylhexyl methoxycinnamate | 6% by weight (Neo Heliopan AV) |
| | Sodiumphenyl benzimidazole sulfonate | 2% by weight (Neo Heliopan hydro) |
| | Disodiumphenyl dibenzimidazole tetrasulfonate | 2% by weight (Neo Heliopan AP) |
| | Cosmedia DC (Hydrogenated Dimer Dilinoleyl/Dimethylcarbonate Copolymer) | 1% by weight |
| | Xanthan gum | 0.5% by weight |
| | Glycerol | 3% by weight |
| | Water, preservative | 55% by weight |
| 5d. | Sun lotion | |
| | Concentrate formulation 1 | 25% by weight |
| | Dibutyl adipate | 5% by weight |
| | Methylene-bis-benzotriazolyl tetramethyl butyl phenol | 2% by weight (Tinosorb M) |
| | Bis-ethylhexyloxyphenol methoxyphenyltriazine | 2% by weight (Tinosorb S) |
| | Ethylhexyl methoxycinnamate | 6% by weight (Neo Heliopan AV) |
| | Sodiumphenyl benzimidazole sulfonate | 2% by weight (Neo Heliopan hydro) |
| | Disodiumphenyl dibenzimidazole tetrasulfonate | 2% by weight (Neo Heliopan AP) |
| | Cosmedia DC (Hydrogenated Dimer Dilinoleyl/Dimethylcarbonate Copolymer) | 1% by weight |
| | Xanthan gum | 0.5% by weight |
| | Glycerol | 3% by weight |
| | Water, preservative | 51.5% by weight |
| 5e. | Sun cream | |
| | Concentrate formulation 2 | 25% by weight |
| | Dibutyl adipate | 5% by weight |
| | Octocrylene | 2% by weight |
| | Methyl benzylidene | 2% by weight (Neo Heliopan MBC) |
| | Ethylhexyl methoxycinnamate | 6% by weight (Neo Heliopan AV) |
| | Cosmedia DC (Hydrogenated Dimer Dilinoleyl/Dimethylcarbonate Copolymer) | 1% by weight |
| | Sodium polyacrylate | 1.2% by weight |
| | Glycerol | 3% by weight |
| | Water, preservative | 54.8% by weight |

6. Application for Insect Repellent Concepts

| 6a. | Insect repellent lotion | |
|---|---|---|
| | Concentrate formulation 4 | 25% by weight |
| | Dicaprylyl ether | 5% by weight |
| | Sodium polyacrylate | 0.5% by weight |
| | N,N-diethyl-m-toluene amide | 2% by weight |
| | Glycerol | 3% by weight |
| | Water, preservative | 64.5% by weight |

What we claim is:

1. An emulsion concentrate comprising:
   (a) 3 to 5% by weight lauryl glucoside,
   (b) 1 to 2% by weight myristyl glucoside,
   (c) 5 to 7% by weight polyglycerol-2-dipolyhydroxystearate,
   (d) 4 to 8% by weight of a $C_{12-24}$ fatty alcohol,
   (e) 70 to 75% by weight of an oil component,
   (f) 4 to 5% by weight of a hydrotrope selected from the group consisting of a diol, a polyol and a glycerol, and mixtures thereof; and
   (g) 2 to 10% by weight water.

2. The emulsion concentrate of claim 1, wherein the emulsion has a viscosity at 23° C. of less than 2,000 mPa·s, as measured with a Brookfield RVF viscosimeter, spindle 5, 10 r.p.m.

3. The emulsion concentrate of claim 1 wherein the emulsion is transparent.

4. The emulsion concentrate of claim 1 wherein the emulsion has a mean droplet size of less than 100 nm.

5. The emulsion concentrate of claim 4 wherein the mean droplet size is less than 50 nm.

6. The emulsion concentrate of claim 5 wherein the mean droplet size is less than 10 nm.

7. The emulsion concentrate of claim 1 wherein the $C_{12-24}$ fatty alcohol is a cetyl alcohol, a stearyl alcohol or a combination thereof.

8. The emulsion concentrate of claim 1 wherein the hydrotrope is glycerol.

9. An emulsion concentrate comprising:
(a) 3 to 5% by weight lauryl glucoside,
(b) 1 to 2% by weight myristyl glucoside,
(c) 5 to 7% by weight polyglycerol-2-dipolyhydroxystearate,
(d) 4 to 8% by weight of stearyl alcohol or cetyl alcohol, or a combination thereof.
(e) 70 to 75% by weight of an oil component,
(f) 4 to 5% by weight of glycerol; and
(g) 2 to 10% by weight water.

10. A cosmetic or pharmaceutical composition comprising from 5 to 40% by weight of the emulsion concentrate of claim 1.

11. A cosmetic or pharmaceutical composition comprising from 5 to 40% by weight of the emulsion concentrate of claim 9.

12. A substrate for body care which is treated with the cosmetic or pharmaceutical composition of claim 10.

13. A substrate for body care which is treated with the cosmetic or pharmaceutical composition of claim 11.

14. The emulsion concentrate of claim 1 wherein the emulsion has a mean droplet size of at most 100 nm.

* * * * *